(12) United States Patent
Groves (10) Patent No.: US 8,389,231 B2
(45) Date of Patent: Mar. 5, 2013

(54) ASSAYS, METHOD AND COMPOSITIONS THAT EXPLOIT A MYCOBACTERIAL IRON ACQUISTION PATHWAY IN CELLS

(75) Inventor: John T. Groves, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 796 days.

(21) Appl. No.: 11/990,718

(22) PCT Filed: Aug. 23, 2006

(86) PCT No.: PCT/US2006/032933
§ 371 (c)(1),
(2), (4) Date: Aug. 18, 2009

(87) PCT Pub. No.: WO2007/024960
PCT Pub. Date: Mar. 1, 2007

(65) Prior Publication Data
US 2009/0297647 A1    Dec. 3, 2009

Related U.S. Application Data

(60) Provisional application No. 60/710,531, filed on Aug. 23, 2005, provisional application No. 60/784,984, filed on Mar. 23, 2006.

(51) Int. Cl.
*C12Q 1/00* (2006.01)
*C12Q 1/02* (2006.01)
(52) U.S. Cl. .............................................. 435/29; 435/4
(58) Field of Classification Search .................. None
See application file for complete search history.

(56) References Cited

PUBLICATIONS

Luo et al. "Mycobactin-mediated iron acquisition within macrophages". Nature Chemical Biology. 2005. vol. 1, No. 3, pp. 149-153.*
Byrd, T. F. & Horwitz, M. A., 1993, "Regulation of Transferrin Receptor Expression and Ferritin Content in Human Mononuclear Phagocytes," *Journal of Clinical Investigation*, vol. 91, pp. 969-976.
Chua, J. et al., 2004, "A Tale of Two Lipids: *Mycobacterium tuberculosis* Phagosome Maturation Arrest," *Current Opinion in Microbiology*, vol. 7:, pp. 71-77.
Crosa, J. H. & Walsh, C. T., 2002, Genetics and Assembly Line Enzymology of Siderophore Biosynthesis in Bacteria, *Microbiology and Molecular Biology Reviews*, vol. 66, pp. 223-249.
David, S. et al., 2005, "In Vitro Effect of Free and Complexed Indium (III) Against *Mycobacterium tuberculosis*," *FEMS Microbiol. Lett*, vol. 251, pp. 119-124.
De Voss, J. J. et al., 1999, "Iron Acquisition and Metabolism by Mycobacteria," *Journal of Bacteriology*, vol. 181, pp. 4443-4451.
De Voss, J. J. et al., 2000; "The Salicylate-Derived Mycobactin Siderophores of *Mycobacterium tuberculosis* are Essential for Growth in Macrophages," *Proceedings of the National Academy of Sciences USA*, vol. 97, pp. 1252-1257.
Dvorak, A.M. et al., 1983, "Lipid Bodies: Cytoplasmic Organelles Important to Arachidonate Metabolism in Macrophages and Mast Cells," *J. Immunol.* vol. 131, pp. 2965-2976.
Fadeev et al., 2005, " Synthesis and Structural Modeling of the Amphiphillic Siderophore Rhizobactin 1021 and its Analogs," *Bioorg. Med. Chem. Lett.* vol. 15, pp. 3771-3774.
Fluckinger, M. et al., 2004, "Human Tear Lipocalin Exhibits Antimoicrobial Activity by Scavenging Microbial Siderophores," *Antimicrobial Agents and Chemotherapy*, vol. 48, pp. 3367-3372.
Goetz, D. H. et al., 2002, "The Neutrophil Lipocalin NGAL is a Bacteriostatic Agent that Interferes with Siderophore-Mediated Iron Acquisition," *Molecular Cell*, vol. 10, pp. 1033-1043.
Hentze, M. W. et al., 2004, "Balancing Acts: Molecular Control of Mammalian Iron Metabolism," *Cell*, vol. 117, pp. 285-297.
Luo et al., 2005, "Membrane Dynamics of the Amphiphillic Siderophore, Acinetoferrin," *J. Am. Chem.* vol. 127, pp. 1726-1736.
Melo, R.C.N. et al., 2003, "Macrophage Lipid Body Induction by Chagas Disease in Vivo: Putative Intracellular Domains for Eicosanoid Formation During Infection," *Tissue Cell*, vol. 35, pp. 59-67.
Moody, D.B. et al., 2004, "T Cell Activation by Lipopeptide Antigens," *Science*, vol. 303, pp. 527-531.
Mulero, V. & Brock, J.H., 1999, "Regulation of Ron Metabolism in Murine J774 Macrophages: Role of Nitric Oxide-Dependent and -Independent Pathways Following Activation with Gamma Interferon and Lipopolysaccharide," *Blood* vol. 94, pp. 2383-2389.
Murphy, D.J., 2001, "The Biogenesis and Functions of Lipid Bodies in Animals, Plants and Microorganisms," *Prog. Lipid Res.* vol. 40, pp. 325-438.
Olakanmi, O. et al., 2000, "Gallium Disrupts Iron Metabolism of Mycobacteria Residing Within Human Macrophages," *Infect. Immun.*, vol. 68, pp. 5619-5627.
Olakanmi, O. et al., 2002, "Intraphagosomal *Mycobacterium tuberculosis* Acquires Iron from Both Extracellular Transferrin and Intracellular Iron Pools," *Journal of Biological Chemistry*, vol. 77, pp. 49727-49734.
Pieters, J., 2001, "Entry and Survival of Pathogenic Mycobacteria in Macrophages," *Microbes and Infection*, vol. 3, pp. 249-255.
Ratledge, C. & Dover, L. G., 2000, "Iron Metabolism in Pathogenic Bacteria," *Annual Review of Microbiology*, vol. 54, pp. 881-941.
Ratledge, C., 2004 "Iron, Mycobacteria and Tuberculosis," *Tuberculosis*, vol. 84, pp. 110-130.
Regoeczi, E. et al., 1995, "Cobalt(III)-Transferrin: Production and Some of its Properties," *Analyst* vol. 120, pp. 733-736.
Rhoades, E. R. & Ullrich, H. J., 2000, "How to Establish a Lasting Relationship with Your Host: Lessons Learned from *Mycobacterium* Spp," *Immunology and Cell Biology*, vol. 78, pp. 301-310.
Snow, G.A., "Isolation and Structure of Mycobactin T, a Growth Factor from *Mycobacterium tuberculosis*," *Biochem. J.*, vol. 97, pp. 166-175.
Sun, H.Z. et al., 1999, "Transferrin as a Metal Ion Mediator," *Chem. Rev.* vol. 99, pp. 2817-2842.

(Continued)

*Primary Examiner* — Vera Afremova
(74) *Attorney, Agent, or Firm* — Potter Anderson & Corroon, LLP (57) ABSTRACT

Assays for the identification of antibacterial agents that inhibit mycobacterial growth by interfering with the iron acquisition pathway in host cells are disclosed. Also disclosed are methods of inhibiting mycobacterial growth by interfering with iron uptake or by delivering antibacterial agents to mycobacteria in host cells through the iron uptake pathway, as well as certain compounds that are useful in the assay methods, and also as antibacterial agents.

9 Claims, 4 Drawing Sheets

PUBLICATIONS

Torti, S. V. et al., 1988, "The Molecular cloning and Characterization of Murine Ferritin Heavy Chain, a Tumor Necrosis Factor-Inducible Gene," *Journal of Biological Chemistry*, vol. 263, pp. 12638-12644.

Weiss, G. et al., 1995, "Linkage of Cell-Mediated Immunity to Iron Metabolism," *Immunology Today* vol. 16, pp. 495-500.

Xu, G.F. et al., 2002, "Membrane Affinity of the Amphiphillic Marinobactin Siderophores," *J. Am. Chem. Soc.* vol. 124, pp. 13415. 13408.

Yu, W.G. et al., 1998, "Co-Compartmentalization of MAP Kinases and Cytosolic Phospholipase $A_2$ at Cytoplasmic Arachidonate-Rich Lipid Bodies," *Am. J. Pathol.* vol. 152, pp. 759-769.

Luo, Minkui et al., "Mycobactin-Mediated Iron Acquisition Within Macrophages," *Nature Chemical Biology*, [Online], vol. 1(3), Jul. 3, 2005 (205-07-03), pp. 149-153, XP002424087, ISSN: 1552-4450 (print) 1552-4469(ele, retrieved from the Internet: URL: www.nature.cominchembio/journal/vl/n3/pdfinchembio717.pdf. [retrieved on Mar. 12, 2007], the whole document.

Devoss, J.J. et al., "The Salicylate-Derived Mycobactin Siderophores Tuberculosis are Essential for Growth in Macrophages," *Proceedings of the National Academy of Sciences of the United States of America*, vol. 97(3), Feb. 1, 2000, pp. 1252-1257, XP002424088, ISSN: 0027-8424, p. 1256, col. 2, paragraph 3.

Snow, G.A., "Metal Complexes of Mycobactin P and of Desferrisideramines," *The Biochemical Journal*, Nov. 1969, vol. 115(2), Nov. 1969, pp. 199-205, XP00242089, ISSN: 0264-6021, abstract.

Olakanmi, O. et al., "Gallium Disrupts Iron Metabolism of Mycobacteria Residing Within Human Macrophages," *Infection and Immunity*, vol. 68(10), Oct. 2000, pp. 5619-5626, XP002424090, ISSN: 0019-9567, p. 5625, col. 1, paragraph 2.

Xu, Guofeng, et al., "Membrane Affinity of the Amphiphilic Marinobactin Siderophores"; J. Am. Chem. Soc., vol. 124, pp. 13408-13415 (2002).

\* cited by examiner

ASSAYS, METHOD AND COMPOSITIONS THAT EXPLOIT A MYCOBACTERIAL IRON ACQUISTION PATHWAY IN CELLS

This claims benefit of U.S. Provisional Application No. 60/710,531, filed Aug. 23, 2005, and U.S. Provisional Application No. 60/784,984, filed Mar. 23, 2006, the entire contents of each of which are incorporated by reference herein.

Pursuant to 35 U.S.C. §202(c), it is acknowledged that the United States Government may have rights in the invention described herein, which was made in part with funding from the National Science Foundation, Grant No. 9810248.

FIELD OF THE INVENTION

This invention relates to the fields of bacteriology and drug discovery. In particular, the invention features assays for the identification of antibacterial agents that inhibit mycobacterial growth by interfering with the iron uptake pathway. The invention also features methods of inhibiting mycobacterial growth by interfering with iron uptake or by delivering antibacterial agents through the iron uptake pathway, as well as certain compounds that are useful in the assay methods, and also as antibacterial agents.

BACKGROUND OF THE INVENTION

Various publications, including patents, published applications, technical articles and scholarly articles are cited throughout the specification. Each of these cited publications is incorporated by reference herein, in its entirety. Full citations for publications referenced by number in the specification are set forth at the end of the specification.

Macrophages stand as gatekeepers in the host immune defense against invading bacteria due to their rich array of antimicrobial devices. While macrophages can internalize a variety of intruding microbes through phagocytosis and degrade them within phagolysosomes, pathogenic mycobacteria have developed creative means to avoid the fatal fusion with lysosomes, and successfully multiply within these structures (Rhoades, E. R. & Ullrich, H. J., 2000, *Immunology and Cell Biology* 78: 301-310; Pieters, J., 2001, *Microbes and Infection* 3: 249-255; Chua, J. et al., 2004, *Current Opinion in Microbiology* 7: 71-77).

*Mycobacterium tuberculosis*, one of the most serious macrophage-targeted pathogens, currently infects one third of the world's population and increasing reports of multi-drug resistant *tuberculosis* (MDR-TB) further threaten TB control efforts (World Health Organization tuberculosis fact sheet: see worldwide web url at int/mediacentre/factsheets). *M. avium* and *M. tuberculosis* are also a growing problem for HIV patients.

Iron is an essential element for both hosts and bacterial pathogens due to its central role in a variety of metabolic pathways (Ratledge, C. & Dover, L. G., 2000, *Annual Review of Microbiology* 54: 881-941; Hentze, M. W. et al., 2004, *Cell* 117: 285-297). Consequently, restricting the availability of iron is an important defense against bacterial infection. Among the various strategies adapted by human for this purpose are the increased synthesis of ferritins (Weiss, G. et al., 1995, *Immunology Today* 16: 495-500; Byrd, T. F. & Horwitz, M. A., 1993, *Journal of Clinical Investigation* 91: 969-976), the withdrawal of iron from serum transferring (Torti, S. V. et al., 1988, *Journal of Biological Chemistry* 263: 12638-12644), and the secretion of lipocalins to scavenge microbial siderophores (Goetz, D. H. et al., 2002, *Molecular Cell* 10: 1033-1043; Fluckinger, M. et al., 2004, *Antimicrobial Agents and Chemotherapy* 48: 3367-3372). Even in the face of these defenses, pathogenic mycobacteria do gain sufficient iron for growth while residing within phagosomes (Ratledge et al., 2000, supra; Ratledge, C., 2004 *Tuberculosis* 84: 110-130; Olakanmi, O. et al., 2002, *Journal of Biological Chemistry* 277: 49727-49734). This observation suggest that mycobacteria must successfully circumvent these host iron restrictions.

In vitro, pathogenic mycobacteria secrete two classes of iron chelating agents, known as siderophores: water-soluble carboxymycobactins and lipophilic mycobactins, which are responsible for extracellular iron transport to the bacteria (Crosa, J. H. & Walsh, C. T., 2002, *Microbiology and Molecular Biology Reviews* 66: 223-249; De Voss, J. J. et al., 1999, *Journal of Bacteriology* 181: 4443-4451). Recent studies indicate that liphophilic mycobactins are essential for the iron access and transport of macrophage-niched mycobactria (De Voss, J. J. et al., 2000; *Proceedings of the National Academy of Sciences USA* 97: 1252-1257). However, little is known about the iron acquisition and transport pathways adapted by mycobacteria in vivo.

Elucidating and exploiting the mechanisms of virulent mycobacterial pathology to develop new approaches to combating these infections are of urgent concern to world health care. There is an ongoing need for new biological targets for the rational design of antibacterial agents, as well as screening methods for identifying and testing candidate compounds, and thereafter developing new methods and agents for the treatment of mycobacterial infection.

SUMMARY OF THE INVENTION

One aspect of the invention features a method of identifying compounds that interfere with mycobactin-mediated iron acquisition by mycobacteria within phagosomes of host cells, wherein interference with the mycobactin-mediated iron acquisition results from interference with one or more of: transport of apo-mycobactin across phagosome membranes into the host cytoplasm, formation of ferric mycobactin complexes in the host cytoplasm, accumulation of ferric mycobactin complexes in lipid droplets, or delivery of ferric mycobactin complexes to phagosomes from lipid droplets. The method comprises the steps of: (a) exposing host cells, in the presence or absence of a test compound, to a mycobactin component selected from apo-mycobactin, ferric mycobactin complex, or a ferric mycobactin complex analog or derivative that binds to lipid droplets, under conditions that, in the absence of the test compound, would permit entry of the mycobactin component into the host cell cytoplasm, formation of ferric mycobactin complexes within the host cells, accumulation of ferric mycobactin complexes in lipid droplets and delivery of ferric mycobactin complexes to phagosomes from lipid droplets; and (b) measuring the amount of one or more of: (i) mycobactin components present in the host cytoplasm; (ii) ferric mycobactin complexes formed from apo-mycobactin; (iii) ferric mycobactin complexes or ferric mycobactin complex analogs or derivatives associated with lipid droplets; and (iv) ferric mycobactin complexes or ferric mycobactin analogs or derivatives present within phagosomes; a decrease in any of (i)-(iv) in the presence of the test compound, as compared with in the absence of the test compound, being indicative that the test compound interferes with mycobactin-mediated iron acquisition by mycobacteria within phagosomes of host cells.

In this aspect of the invention, the host cells may macrophage or macrophage-like cells, and typically are cultured cells. The mycobactin component can mycobactin J or mycobactic acid J, or other mycobactins and related molecules as described in greater detail herein. Preferably, the mycobactin component is detectable, for example, a mycobactin complex analog or derivative selected from gallium-mycobactin or gallium-mycobactic acid.

In certain embodiments, the mycobactin component is apo-mycobactin and the amount of apo-mycobactin together with ferric mycobactin complex within host cells is measured to provide a total amount of mycobactin components in the host cells, wherein a decrease in the total amount of mycobactin components in the presence of the test compound, as compared with in the absence of the test compound, is indicative that the test compound can interfere with transport of apo-mycobactin across phagosome membranes into the host cytoplasm.

In other embodiments, the mycobactin component is apo-mycobactin and the amount of ferric mycobactin complex within host cells is measured, wherein a decrease in amount of ferric mycobactin complex in the presence of the test compound, as compared with in the absence of the test compound, is indicative that the test compound interferes with formation of ferric mycobactin complexes in host cells.

In other embodiments, the mycobactin component is a ferric mycobactin complex or a ferric mycobactin complex analog or derivative that binds to lipid droplets, and the amount of ferric mycobactin complex or ferric mycobactin complex analog or derivatives accumulated in the lipid droplets is measured, wherein a decrease in the amount of ferric mycobactin complex or ferric mycobactin complex analog or derivatives accumulated in the lipid droplets in the presence of the test compound, as compared with in the absence of the test compound, is indicative that the test compound interferes with accumulation of ferric mycobactin complexes in host cell lipid droplets.

In still other embodiments, the mycobactin component is a ferric mycobactin complex or a ferric mycobactin complex analog or derivative that binds to lipid droplets, and the amount of ferric mycobactin complex or ferric mycobactin complex analog or derivatives delivered to phagosomes is measured, wherein a decrease in the amount of ferric mycobactin complex or ferric mycobactin complex analog or derivatives delivered to phagosomes in the presence of the test compound, as compared with in the absence of the test compound, is indicative that the test compound interferes with delivery of ferric mycobactin complexes from the lipid droplets to the phagosomes.

Another aspect of the invention features a method of identifying compounds that inhibit growth of mycobacteria in host cells by interfering with mycobactin-mediated iron acquisition by the mycobacteria within phagosomes of the host cells. The method comprises the steps of: (a) measuring mycobacterial growth in the host cells in the presence or absence of a test compound; (b) exposing the host cells, in the presence or absence of the test compound, to a mycobactin component selected from apo-mycobactin, ferric mycobactin complex, or a ferric mycobactin complex analog or derivative that binds to lipid droplets, under conditions that, in the absence of the test compound, would permit entry of the mycobactin component into the host cell cytoplasm, formation of ferric mycobactin complexes within the host cells, accumulation of ferric mycobactin complexes in lipid droplets and delivery of ferric mycobactin complexes to phagosomes from lipid droplets; and (c) measuring the amount of one or more of: (i) mycobactin components present in the host cytoplasm; (ii) ferric mycobactin complexes formed from apo-mycobactin; (iii) ferric mycobactin complexes or ferric mycobactin complex analogs or derivatives associated with lipid droplets; and (iv) ferric mycobactin complexes or ferric mycobactin analogs or derivatives present within phagosomes. A decrease in mycobacterial growth combined with a decrease in any of (i)-(iv) in the presence of the test compound, as compared with in the absence of the test compound, is indicative that the test compound inhibits mycobacterial growth by interfering with mycobactin-mediated iron acquisition by the mycobacteria within phagosomes of the host cells. In certain embodiments, host cells are macrophage or macrophage-like cells. The host cells are cultured cells or, alternatively, at least the step measuring mycobacterial growth in the host cells in the presence or absence of a test compound is performed on host cells disposed within a living organism. In certain embodiments, the mycobactin component is mycobactin J or mycobactic acid J, and preferably is detectable, e.g., by fluorescence such as is displayed by gallium-mycobactin or gallium-mycobactic acid. In certain embodiments, the mycobacteria are *Mycobacterium tuberculosum* or *Mycobacterium smegmatis*.

Another aspect of the invention features a method of reducing or preventing mycobactin-mediated iron acquisition by mycobacteria within phagosomes of host cells. This method comprises interfering with one or more of: transport of apo-mycobactin across phagosome membranes into the host cytoplasm, formation of ferric mycobactin complexes in the host cytoplasm, accumulation of ferric mycobactin complexes in lipid droplets, or delivery of ferric mycobactin complexes to phagosomes from lipid droplets, resulting in the reduction or prevention of the mycobactin-mediated iron acquisition by the mycobacteria. The host cells typically are macrophage or macrophage-like cells, and they may be cultured cells or cells disposed within a living organism.

In one embodiment, the method comprises inhibiting or preventing accumulation of ferric mycobactin complexes in the lipid droplets. In another embodiment, the method comprises exposing the host cells to a substance that occupies substantially all ferric mycobactin complex binding locations within the lipid droplets, thereby preventing accumulation of the ferric mycobactin complexes in the lipid droplets. In a particular embodiment, the substance is a gallium-mycobactin complex, a gallium-mycobactic acid complex, or a gallium-acinetoferrin complex. Alternatively, the substance is an indium-mycobactin complex or derivative thereof.

In certain embodiments, the method results in the inhibition of growth of the mycobacteria within the host cells. Optionally, this method can be adapted for practice on a patient and further results in reduction or elimination of a mycobacterial infection in the patient, such as an infection with *Mycobacterium tuberculosis*.

Another aspect of the invention features a method of reducing or alleviating a mycobacterial infection of host cells, comprising exposing the host cells to an antibacterial agent that accumulates in host cell lipid droplets and is thereafter delivered from the lipid droplets to phagosomes containing the mycobacteria, resulting in reduction or alleviation of the mycobacterial infection of the host cells. The host cells typically are macrophage or macrophage-like cells and they may be cultured cells or cells disposed within a living organism. In a particular embodiment, the antibacterial agent is a gallium-mycobactin complex, a gallium-mycobactic acid complex, or a gallium-acinetoferrin complex. Alternatively, the agent is an indium-mycobactin complex or derivative thereof. In a particular embodiment, mycobacterial infection is an infection with *Mycobacterium tuberculosis*.

Another aspect of the invention features an anti-mycobacterial agent which is a gallium derivative of a mycobactin or an acinetoferrin. Alternatively, the agent may be an indium derivative of a mycobactin. In a particular embodiment, the antibacterial agent is selected from a gallium-mycobactin J complex, a gallium-mycobactic acid J complex, or a gallium-acinetoferrin complex.

Various features and advantages of the present invention will be understood by reference to the detailed description, drawings and examples that follow.

BRIEF DESCRIPTION OF THE DRAWINGS

FIG. 1. MJ-mediated iron acquisition. (FIG. 1a) The structure of MJ and Ga-MJ. The oxygen and nitrogen chelating moieties of MJ are marked with arrows. A representative 3-D structure of Ga-MJ with C, dark gray; H, light gray; O, red (or very dark gray for non-color reprints); N, blue (and marked with an X for non-color reprints); Ga, cyan (or larger very light gray sphere in center of molecule for non-color reprints). (FIG. 1b) The conversion to Fe-MJ. MJ targets macrophage-intracellular iron, a process promoted by hTf. Ves, 0.05 mM vesicle; Ves+hTf, 0.05 mM vesicle with 10 µM hTf; Cell, macrophages; Cell+hTf, macrophages supplied with 10 µM hTf. "Net conversion (%)" is the ratio of the actual conversion to Fe-MJ to the theoretical 100% conversion. (FIG. 1d) Co(III)-Tf-stimulated iron acquisition of MJ. All the experiments were carried out similarly as described in FIG. 1b in either the absence ("Cell") or the presence of 10 µM hTf ("hTf"), Co(III)-Tf ("Co-Tf"), Al(III)-Tf ("Al-Tf"), Ga(III)-Tf ("Ga-Tf") or 1 mg/ml bovine serum albumin as the control (BSA). 100% "Relative conversion (%)" was defined as the conversion at 37° C. without hTf. Negative "Relative conversion (%)" corresponds to the less-than-basal recovery of Fe-MJ. Plots show means of triplicates with standard errors (s.e.m).

FIG. 2. Membrane partitioning of MJ and Fe-MJ. FIG. 2a and FIG. 2b show means of triplicates with standard errors (s.e.m).

FIG. 3. Distribution patterns of MJ and Ga-MJ within macrophages. (FIG. 3b, upper right panel series) Identifying the preferential locus as lipid-droplets. The Nile-red-stained lipid-droplets (red channel, if figure is viewed in color) were colocalized with the Ga-MJ-preferred locus (green channel, if figure is viewed in color). Images from the left to right: transmission images of macrophages, Ga-MJ and Nile red. (FIG. 3d, lower right panel series) Co-stain of Ga-MJ and fluorescence-labeled E. coli phagosomes. Arrows marked the contacting regions for Ga-MJ-stained lipid-droplets (green channel if figure is viewed in color) and fluorescence-labeled E. coli phagosomes (red channel if figure is viewed in color). Images from left to right: transmission images of macrophages, Ga-MJ, phagosomes, and the overlap of all the three. The upper right profiles are two representative images of the closeup interaction between Ga-MJ-laden lipid droplets and E. coli-residing phagosomes.

FIG. 4. Diagram of MJ-mediated ferric acquisition pathway for macrophage-niched mycobacteria. Mycobacteria are initially internalized through phagocytosis and reside in phagosomes. The newly-assembled mycobactins diffuse away from mycobacteria and rapidly distribute between bulk medium and cellular lipid components. (1. MJ diffusion). These diffusible mycobactins access intracellular iron pool and mobilize iron there (2. Ferric acquisition). This process is also stimulated by hTf and Co(III)-Tf. Ferric mycobactins then diffuse away from the intracellular iron pool (3. Fe-MJ diffusion). Finally, ferric mycobactins preferentially localize to lipid droplets, where they are ready to be delivered to lipid-droplet-attached, mycobacteria-residing phagosomes (4. Lipid-droplet localization).

DETAILED DESCRIPTION

In its various aspects, the present invention provides methods and compositions for identifying agents that interfere with iron uptake by Mycobacterium tuberculosum and related organisms residing within host cells, as well as compositions methods for inhibiting mycobacterial growth and for treating mycobacterial diseases, such as tuberculosis. Aspects of the invention are developed from the discovery, in accordance with the invention, of a mycobactin-mediated ferric acquisition pathway for mycobacteria residing in macrophages.

Figure 4:
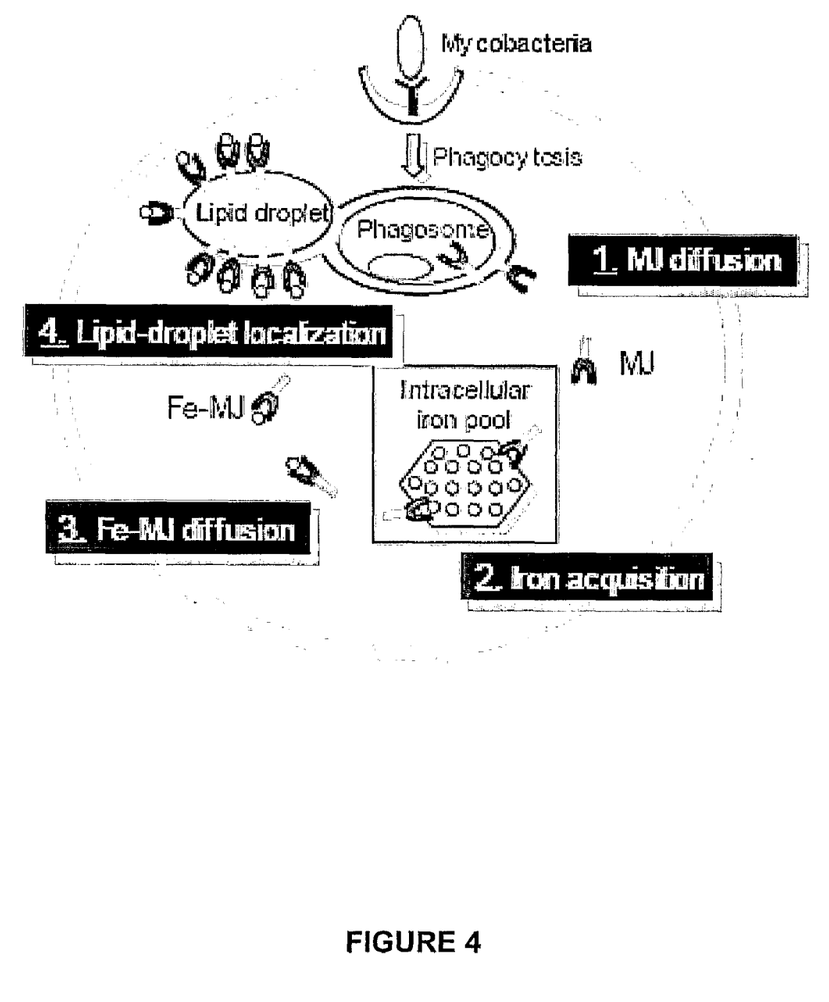

Details of the pathway are shown diagrammatically in FIG. 4. Upon taking residence in early phagosomes through macrophage-mediated phagocytosis, pathogenic mycobacteria assemble mycobactins and the corresponding transport systems via mbtA-J gene products (Crosa, J. H. & Walsh, C. T., 2002, Microbiol. Mol. Biol. Rev. 66: 223-249). The newly synthesized mycobactins then diffuse into the host macrophage (FIG. 4, step 1). Due to the moderate membrane affinity and ready membrane permeability of mycobactins, a dynamic distribution of mycobactins is rapidly built up between the medium and cellular lipid components. Subsequently, mycobactins mobilize iron from the macrophage-intracellular iron pool (step 2). Mycobactins may also acquire iron from endocytosis-internalized transferrin (Olakanmi et al., 2002, supra). It is likely that this pathway becomes dominant for those macrophage cells that have intrinsically low iron storage but are rapidly mobilizing iron from transferrin. Upon chelating iron, mycobactins are converted into ferric mycobactins that also rapidly diffuse through the cellular milieu and reach a dynamic distribution between the medium and cellular lipid components (step 3). Ferric mycobactin is further recruited to lipid droplets delivered via lipid trafficking to the phagosomes (step 4). These properties provide macrophage-ensconced mycobacteria with the mycobactin-mobilized iron. All these observations indicate that the dynamics of iron mobilization, membrane trafficking and lipid sorting within macrophages have been exploited to deliver iron to mycobacteria residing in phagosomes.

The above-described pathway accommodates the results of previous studies of pathogenic mycobacteria and their siderophore products. First, an *M. tuberculosis* mutant incapable of producing mycobactins displays restricted growth both within macrophages and under iron limitation (DeVoss et al., 2000, supra). Therefore, mycobactins must be virulence factors during infection. Secondly, the administration of mycobactins and ferritins, but not either of them alone, promotes the fast growth of *M. tuberculosis* in vitro (Crosa et al., 2002, supra). Both of these results are consistent with MJ-mediated iron acquisition from the macrophage-intracellular iron pool.

Lipophilic mycobactins were previously thought to act as intra-envelope, short-term iron storage molecules by interacting with hydrophilic carboxymycobactins, the latter of which are responsible for extracellular iron acquisition (Ratledge, C., 2004, *Tuberculosis* 84: 110-130). The studies of mycobactin J, as reported in Example 1 herein, indicate that the amphiphile readily acquires macrophage-intracellular iron via membrane diffusion. In particular, the discovery in accordance with the invention that Ga-MJ accumulates in lipid droplets while MJ does not preferentially bind to that site, indicates that lipid droplets are a key locus for iron restriction. Accordingly, aspects of the present invention are directed to agents that target the Ga-MJ binding site, thereby inhibiting transport to mycobacteria. Alternatively, antimicrobial agents may be designed to mimic the mycobactins and accumulate in the lipid droplets. As described in greater detail below, mycobactin gallium complexes themselves, as well as gallium complexes of other siderophores, are expected to be useful for this purpose because they can deliver gallium specifically to intracellular mycobacteria instead of other host cells, at which point the gallium is capable of disrupting mycobacterial iron metabolism (Olakanmi, O. et al., 2000, *Infect. Immun.* 68: 5619-5627).

The following sections describe details of these and other aspects of the invention. Unless specifically stated otherwise, standard, commercially available reagents and methodologies, familiar to those of skill in the art, are utilized in the practice of the present invention.

Assays

The elucidation, in accordance with the present invention, of a mycobactin-mediated iron acquisition pathway in host cells inhabited by mycobacteria provides an underpinning for a variety of cell-based and other assays for identifying antibacterial agents that target this pathway. Following internalization of the mycobacteria by phagocytosis, the pathway involves (1) diffusion of newly-formed mycobactins away from the mycobacteria, (2) accession of the diffusible mycobactins to the intracellular iron pool and mobilization of the iron there, (3) diffusion of the ferric mycobactins away from the intracellular iron pool, and (4) localization of the ferric mycobactins to lipid droplets, which subsequently migrate to phagosomes residing in the mycobacteria and deliver the ferric mycobactins.

In many embodiments, the assays described hereinbelow are carried out in cultured cells. Suitable cell types for use in such assays include, but are not limited to, macrophage or macrophage-like cells, or other immune-type cells as would be understood by the skilled artisan (e.g., foam cells, which may arise from macrophages or smooth muscle cells). Examples of such cell types include the THP-1 cell line (a macrophage-like monocyte), which may be purchased from the American Type Culture Collection.

In certain embodiments, assays are carried out on cells infected with mycobacteria or related strains of bacteria. For example, the non-pathogenic *Mycobacterium smegmatis* (a common soil bacterium, strains of which are available from the American Type Culture Collection) is suitable for use in various of the assays described below, and further to assess the effect of test compounds on mycobacterial growth.

In other embodiments, uninfected cells are utilized, and mycobactins or derivatives and analogs thereof are supplied exogenously. Mycobactins suitable for use in the present invention include mycobactin-J (from *Mycobacterium paratuberculosis*), which is exemplified herein, as well as other mycobactins from several other species of *Mycobacterium*. These include, but are not limited to, mycobactin A (*M. aurum*), mycobactins F and H (*M. fortuitum*), mycobactins M and N (*M. marinum*), mycobactin R (*M. terrae*), mycobactin S (*M. smegmatis*), mycobactin T (*M. tuberculosis*), mycobactin Av (found in *M. avium, M. intracellulare, M. scrofulaceum* and *M. paratuberculosis*) and mycobactin NA (*Nocardia asteroides*).

In certain assays, apo-mycobactin may be supplied exogenously. In other assays, ferric mycobactin may be supplied exogenously. In other assays, a mycobactin derivative comprising a ferric substitute may be utilized. Of particular utility in this regard are gallium derivatives of mycobactin or mycobactic acid. Other metal derivatives of mycobactin or mycobactic acid suitable for use in the invention include indium, scandium or yttrium derivatives. Additionally, other siderophores having properties similar to mycobactins may be utilized. Particularly suitable are siderophores that can be derivatized with gallium or similar metals (e.g., indium, scandium and yttrium), including for example, acinetoferrins (Fadeev et al., 2004, J. Am Chem. Soc. 126: 12065-12075) and rhizobactins (Fadeev et al., 2005, Bioorg. Med. Chem. Lett. 15: 3771-3774). With respect to acinetoferrins in particular, it has been shown that these siderophores possess membrane dynamics and ferric acquisition features that are similar to those of mycobactins (Luo et al., 2005, J. Am. Chem. Soc. 127: 1726-1736), making them particularly attractive for use in the assays and other methods described herein.

The aforementioned reagents are referred to collectively herein as "mycobactin components," even though they may include siderophores that are not mycobactins. Exemplary reagents used in the assays and other methods of the invention are gallium-mycobactin J (Ga-MJ) and gallium-mycobactic acid J (Ga-MaJ). Methods of making Ga-MJ and Ga-MaJ are set forth in Example 1 and Example 3 herein.

In preferred embodiments, the mycobactin components are detectable by some means, such as by fluorescence or radioactivity, for example. In this regard, it is noteworthy that lipid-phase gallium-mycobactin complexes exhibit pronounced fluorescence. Other metal-mycobactin complexes (e.g., comprising indium, scandium or yttrium instead of gallium) are also expected to be detectable by fluorescence.

One category of assays featured in accordance with the present invention is used to identify agents that interfere with mycobactin-mediated iron acquisition by mycobacteria within phagosomes of host cells. These assays may be customized to pinpoint various steps in the mycobacterial ferric acquisition pathway, namely: (1) diffusion of apo-mycobactin across phagosome or plasma membranes into the host cytoplasm, (2) formation of ferric mycobactin complexes in the host cytoplasm, (3) accumulation of ferric mycobactin complexes in lipid droplets, or (4) delivery of ferric mycobactin complexes to phagosomes from lipid droplets.

(1) In one type of assay, candidate antibacterial agents are screened for their ability to prevent diffusion of apo-mycobactins into the host cellular milieu. Cultured host cells are incubated with exogenously supplied apo-mycobactin in the presence or absence of a test compound, and total mycobactin accumulated in the cells is measured by standard means, such as those described in Example 1. If the test compound acts by inhibiting transport of the apo-mycobactin across cell membranes and into the cytoplasm, then less mycobactin should be accumulated in cells in the presence of the test compound than in the absence of the test compound.

(2) In another type of assay, candidate agents are screened for their ability to inhibit or prevent the formation of ferric mycobactin from apo-mycobactin. In one assay, cultured host cells are incubated with exogenously supplied apo-mycobactin in the presence or absence of a test compound, and ferric mycobactin accumulated in the cells is measured by standard means, such as those described in Example 1. In another assay, the cultured host cells are pre-infected with a mycobacterium that produces apo-mycobactin, which diffuses from the phagosome into the cellular milieu. If the test compound acts by inhibiting the formation of ferric mycobactin, then less ferric mycobactin should be present in cells incubated with test compound than in the absence of the test compound. In particular embodiments, the ratio of ferric mycobactin to apo-mycobactin in the cells can also be measured. If an accumulation of apo-mycobactin is observed, but ferric mycobactin is decreased in the presence of the test compound, it can be concluded that the test compound acts specifically at the step of iron loading of the mycobactin.

(3) In a preferred type of assay, candidate anti-mycobacterial agents are screened for their ability to interfere with localization of ferric mycobactin to lipid droplets within host cells. A particularly suitable way to carry out such an assay is through the use of a detectable analog of ferric mycobactin, including but not limited to gallium-siderophores and derivatives thereof, such as Ga-MJ, Ga-MaJ, Ga-acinetoferrin and Ga-rhizobactin. Ga-MJ an Ga-MaJ are exemplary analogs of this type, inasmuch as they exhibit strong fluorescence in the lipid phase and can be readily detected by confocal microscopy, as described for instance in Example 1. In this type of assay, cultured host cells are incubated with exogenously supplied ferric mycobactin or detectable analog thereof in the presence or absence of a test compound, and localization of the ferric mycobactin to lipid droplets within the cells is observed. If the test compound acts by inhibiting lipid droplet localization, then less ferric mycobactin should be present in lipid droplets of cells incubated with test compound than in the absence of the test compound. In particular embodiments, the ratio of ferric mycobactin in the general lipid phase to lipid droplet-localized ferric mycobactin can also be measured. An accumulation of ferric mycobactin in the cells without localization to lipid droplets in the presence of the test compound is one indication that the test compound acts specifically at the step of ferric mycobactin binding to lipid droplets.

(4) The assay described above can be carried to the next step by using the same methodology to observe whether candidate compound is able to interfere with the ability of lipid droplets loaded with ferric mycobactin to deliver those molecules to mycobacteria residing in phagosomes. If a test compound inhibits or prevents this step of mycobacterial iron acquisition, then an accumulation of ferric mycobactin in lipid droplets should be observed in the presence of the test compound, but a failure in migration of the lipid droplets to the phagosomes, or unloading of the ferric mycobactin within the phagosomes, should be observable, e.g., by confocal microscopy of fluorescent metal mycobactin analogs, or by some other means (e.g., comparative depletion in radiolabeled iron within the mycobacteria residing in the phagosomes).

Any one of the foregoing assays can be linked to a standard assay for bacterial viability to identify candidate antibacterial agents that inhibit growth of mycobacteria in host cells by interfering with mycobactin-mediated iron acquisition by the mycobacteria within phagosomes of the host cells. As one non-limiting example, cultured macrophage or macrophage-like cells can be infected with a mycobacterium, for instance the non-pathogenic *M. smegmatis*, and then incubated with a detectable ferric mycobactin analog, such as Ga-MJ, in the presence or absence of the test compound. A decrease in growth or viability of the bacteria, concomitant with, e.g., a decrease in lipid droplet binding and/or delivery of the Ga-MJ to phagosomes, indicates that the test compound inhibits mycobacterial growth by interfering with those steps in the iron acquisition pathway.

Methods of Controlling Mycobacteria in Host Cells

As mentioned above, the discovery in accordance with the invention that Ga-MJ accumulates in lipid droplets while MJ does not preferentially bind to that site, indicates that lipid droplets are a key locus for iron restriction, via binding of ferric mycobactin for subsequent delivery to phagosomes. Accordingly, aspects of the present invention are directed to agents that target the ferric mycobactin binding locations in lipid droplets, thereby inhibiting transport to mycobacteria. Alternatively, antimicrobial agents may be designed to mimic the mycobactins and follow the same iron acquisition pathway from and back to the phagosomes. Such agents comprise two components—a mycobactin mimicking component and a toxic component that, once delivered to mycobacteria within phagosomes, kills the mycobacteria or otherwise inhibits their viability.

Thus, in another aspect of the invention, methods are provided to reduce or prevent mycobactin-mediated iron acquisition by mycobacteria within phagosomes of host cells. The methods comprise interfering with one or more of: transport of apo-mycobactin across phagosome membranes into the host cytoplasm, formation of ferric mycobactin complexes in the host cytoplasm, accumulation of ferric mycobactin complexes in lipid droplets, or delivery of ferric mycobactin complexes to phagosomes from lipid droplets, resulting in the reduction or prevention of the mycobactin-mediated iron acquisition by the mycobacteria. As mentioned above, a preferred embodiment of this method is the interference with lipid droplet binding, e.g., by saturating ferric mycobactin binding sites on lipid droplets with a ferric mycobactin mimic that itself cannot deliver iron to the phagosome, and prevents the lipid droplets from accumulating ferric mycobactin. The use of such agents is expected to have a bacteriocidal or bacteriostatic effect in mycobacterium-infected cells, due to the interference with iron acquisition by the mycobacteria. In this regard, it should be noted that the method can be practiced on cultured cells, or in vivo on infected cells within a living organism. Furthermore, such methods are expected to be adaptable for practice on a patient and further resulting in reduction or elimination of a mycobacterial infection in the patient. *Mycobacteria* within macrophage phagosomes have limited access to cellular iron stores due to the phagosomal membrane barrier. Lipid droplets are known to be employed by macrophage cells to import lipids, eicosinoids and proteins to the developing phagosome. Since metal-mycobactin complexes have been shown to bind strongly to lipid droplets and since lipid droplets rich in metal-mycobactin complex have been observed in the assays herein to be in contact with 
phagosomes, it is clearly expected that this lipid import pathway will also transport metal-mycobactin complexes to the phagosomes that harbor the mycobacteria.

Of particular utility in these methods are gallium derivatives of mycobactin or mycobactic acid, inasmuch as they have been shown to bind robustly to lipid droplets within macrophage cells. Other metal-mycobactin derivatives as described above may also be utilized for this purpose. Additionally, other gallium-siderophores having properties similar to mycobactins may be utilized, e.g., acinetoferrins.

Another aspect of the invention features a method of reducing or alleviating a mycobacterial infection of host cells by utilizing the mycobacterial iron acquisition pathway to deliver a toxic substance directly to mycobacteria residing in phagosomes. Such antimicrobial agents may be designed to mimic the mycobactins and accumulate in the lipid droplets for subsequent delivery of their toxic component to the phagosome-localized mycobacteria. As mentioned above, mycobactin gallium complexes themselves, as well as gallium complexes of other siderophores, are particularly suitable for this purpose because they can deliver gallium specifically to intracellular mycobacteria instead of other host cells. Gallium itself has been shown to be toxic to mycobacteria by disrupting iron metabolism (Olakanmi et al., 2000, supra). Indium-mycobactin complexes are suitable for this purpose as well, inasmuch as indium(III) has also been shown to inhibit the growth of mycobacteria (David, S. et al., 2005, *FEMS Microbiol. Lett.* 251: 119-124). As above, such methods may be practiced on cultured cells or on cells are disposed within a living organism, such as a patient suffering from a mycobacterial infection.

Antibacterial Agents

As discussed above, gallium derivatives of mycobactin, mycobactic acid and other siderophores having properties similar to mycobactin, are useful not only as reagents for the assays described above, but also as anti-mycobacterial agents themselves. This is due to at least two properties of such compounds. First, their ability to mimic ferric mycobactin in the cellular mycobactin-mediated iron acquisition pathway enables their use to saturate the pathway (particularly lipid droplet binding), thereby preventing the pathway to be used for iron delivery to phagosome-ensconced mycobacteria. Second, these gallium mimics can be toxic in and of themselves due to gallium's ability to interfere with mycobacterial iron metabolism. Accordingly, another aspect of the present invention features these gallium siderophore derivatives as anti-mycobacterial agents. In one specific embodiment, gallium-mycobactin J is utilized as an antibacterial agent. In another specific embodiment, gallium-mycobactic acid J is utilized. Other embodiments are directed to gallium derivatives of other mycobactins, as well as acinetoferrin or rhizobactin. Yet other embodiments are directed to indium derivatives of mycobactins and other siderophores, inasmuch as indium(III) has also been shown to inhibit mycobacterial growth (David et al., 2005, supra) and are expected to possess physico-chemical properties similar to ferric or gallium mycobactins.

The above-described antibacterial agents can be formulated in pharmaceutical compositions for the treatment of mycobacterial infection in accordance with standard protocols used by medicinal chemists. See generally Remington: The Science and Practice of Pharmacy, (formerly called Remington's Pharmaceutical Sciences), Mack Publishing Co., Easton, Pa. (Remington). A pharmaceutical composition as contemplated herein comprises an antibacterial substance as described above, optionally in combination with one or more other therapeutic agents (e.g., Isoniazid, Rifampin, Pyrazinamide, Ethambutol), and a pharmaceutically acceptable carrier.

The form and nature of the pharmaceutically acceptable carrier is controlled by the amounts of the active ingredient to which it is combined, the route of the administration, and other well-known variables. As used herein, the term "carrier" refers to diluents, excipients and the like for use in preparing admixtures of a pharmaceutical composition. The term "pharmaceutically acceptable" means approved by a regulatory agency of the Federal or a state government or listed in the U.S. Pharmacopeia or other generally recognized pharmacopeia for use in humans. Such pharmaceutically acceptable carriers or diluents and methods for preparing are well known in the art (see, e.g., Remington, supra; the Handbook of Pharmaceutical Excipients, APHA publications, 1986).

Pharmaceutically acceptable carriers may be, for example, a liquid or solid. Liquid carriers include, but are not limited, to water, saline, buffered saline, dextrose solution, preferably such physiologically compatible buffers as Hank's or Ringer's solution, physiological saline, a mixture consisting of saline and glucose, and heparinized sodium-citrate-citric acid-dextrose solution and the like, preferably in sterile form. Exemplary solid carrier include agar, acacia, gelatin, lactose, magnesium stearate, pectin, talc and like.

Pharmaceutical compositions may be formulated for parenteral administration (e.g., intravenous, subcutaneous or intramuscular injection). For parenteral administration, the carrier preferably comprises water, saline, alcohol, a lipid, a wax or a buffer.

In some of the embodiments, the compositions can be administered orally. For such administrations, the pharmaceutical composition may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets, capsules or pellets prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

For buccal administration, the compositions may take the form of tablets, troche or lozenge formulated in conventional manner. Compositions for oral or buccal administration, may be formulated to give controlled release of the active compound. Such formulations may include one or more sustained-release agents known in the art, such as glyceryl mono-stearate, glyceryl distearate and wax.

Further, the pharmaceutical composition can be administered nasally or by inhalation, which is particularly advantageous for the treatment of tuberculosis. For nasal or inhalation administration, the compositions are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The following examples are provided to describe the invention in greater detail. They are intended to illustrate, not to limit, the invention.

EXAMPLE 1

Mycobactin-Mediated Iron Acquisition Within Macrophages

This example sets forth evidence for a rapid, mycobactin-mediated iron acquisition process and subsequent, mycobactin-specific iron transport within macrophages that exploits the ready membrane permeability, dynamic diffusibility and high iron affinity of these small lipophilic siderophores. This iron acquisition process is stimulated by ferric transferrin or cobalt(III) transferrin, implicating the iron transport apparatus rather than the iron in transferrin itself as the primary target.

Materials and Methods

Materials and reagents. Apo-transferrin (apo-Tf), fully saturated holo-transferrin (hTf) and bovine serum albumin (BSA) were obtained from Sigma and used without further purification. Desferoxime mesylate salt was obtained from Aldrich and its stock solutions were freshly prepared before use. 1,2-Dimyristoyl-sn-glycero-3-phosphocholine (DMPC) was purchased from Avanti Polar Lipids Inc. DMPC small unilamellar vesicles (SUV) were prepared in HEPES buffer (pH=7.4, 100 mM HEPES, 150 mM NaCl in deionized water) as previously described (Xu, G. F. et al., 2002, *J Am. Chem. Soc.* 124, 13408-13415. PRMI1640 medium, fetal bovine serum and penicillin-streptomycin-L-glutamine solution were purchased from American Type Culture Collection (ATCC). Phenol-red-free PRMI1640 medium supplied with $NaHCO_3$ and HEPES buffer were obtained from Sigma for fluorescent confocal experiments. Ferric mycobactin J was purchased from Allied Monitor. Mycobactin J was made from ferric mycobactin J by discharging iron through the methods developed by Snow (1965, *Biochem. J.* 97: 166-175). Stock solutions of both ferric and mycobactin J, 5 mM in DMSO, were stored at −80° C. for future use. Alexa Fluor 488-conjugated *E. coli*, Alexa Fluor 546-conjugated transferrin, FM 4-64 and lysotracker Green DND-26 (Molecular Probe) were used according to their recommended procedures unless indicated otherwise. Co(III)-transferrin was prepared as previously described (Regoeczi, E. et al., 1995, *Analyst* 120, 733-736). Al(III)-transferrin was prepared in Tris-HCl buffer (0.25 M Tris-HCl, 0.1 mM $NaHCO_3$, 150 mM NaCl, pH 8.0) by mixing one equiv. apo transferrin, 10-fold $Al(NO_3)_3$ and nitrilotriacetic acid (the molar ratio 1:1 to $Al^{3+}$ as an auxiliary agent). The subsequent mixture was incubated at 37° C. for 24 h. Al(III)-Tf was eluted through 10 DG column (Bio-Rad) with Tris-HCl buffer (20 mM Tris-HCl, 150 mM NaCl, pH 7.4). The retention time was estimated on the basis of ferric transferrin. Ga(III)-transferrin was prepared similarly except no nitrilotriacetic acid added as the auxiliary agent. The protein concentrations were measured by the Bradford dye-binding procedure (Bio-Rad's protein assay). Ga-MJ was prepared as the following: 30 mg MJ was dissolved in 0.7 mL of $CD_3OD$ in the 5 mm NMR tube and titrated with the saturated $CD_3OD$ solution of gallium acetylacetonate $Ga(acac)_3$ (Sigma) until the uncomplexed MJ $^1$H-NMR signals completely disappeared and a new set of signals developed. Acetylacetone was removed upon the subsequent evaporation and evacuation. The Ga-MJ sample was purified through a short column in the barrel of the 5 cc hypodermic syringe (bed height 5 cm, diameter 1 cm, 60 mesh silica) and eluted with 0-15% methanol/chloroform to give pure Ga-MJ. The chromatographic process could be easily monitored by UV irradiation at 365 nm, since Ga-MJ displays a bright blue fluorescence.

Cell cultures. The THP-1 cell line (a macrophage-like monocyte) was purchased from American Type Culture Collection (ATCC) and used for all protocols. The cells were cultured into PRMI1640 (ATCC) supplemented with 10% fetal bovine serum (ATCC), 2 mM L-glutamine and 0.02 mM penicillin-streptomycin, and maintained at a cell concentration between $2 \times 10^5$ and $1 \times 10^6$ cells/ml at 37° C. in a 5% $CO_2$ air atmosphere by addition of fresh growth medium (as described above) twice per week. Either PRMI1640 or phenol-red-free PRMI1640 was used with the supply of 2 mM L-glutamine and 0.02 mM penicillin-streptomycin, but in the absence of 10% FBS, for the experiments with MJ.

HPLC analysis for Fe-MJ and MJ. Varian ProStar & PrepStar HPLC and a Waters Delta Pak 5μ C18-300 Åcolumn were used with 3:7 $H_2O:CH_3CN$ as eluting solution under all conditions. The intensities of the peak with retention time 43 min at 460 nm were integrated and normalized to the amount of Fe-MJ. Macrophages (final concentration, $1 \times 10^5$ cells/ml) or 0.05 mM DMPC vesicles as controls were preincubated in RPMI 1640 medium at 37° C. for 4 h, followed by the addition of MJ (final concentration, 1.5 μM). The media were incubated for 24 h at various conditions, such as in the presence or absence of hTf, at varied temperatures or in the presence of different concentrations of desferrioxamine mesylate salt. Three aliquots (3×4 ml) of the medium were collected and lysed by dunces. Lipophilic components were extracted into 3.5 ml $CHCl_3$ and the mixture was centrifuged at 2500 r.p.m for 8 min. The organic layer extraction 2.5 ml was subject to a stream of argon to vaporize $CHCl_3$. The dried mixture was dissolved into 400 μl $CH_3CN$, of which 200 μl solutions was injected into HPLC. The peak intensity of 100% conversion to Fe-MJ was obtained by incubating 1.5 μM Fe-MJ into the medium, following the same workup above.

Cell-aqueous-phase distributions of MJ and Fe-MJ. After the conversion from MJ to Fe-MJ, aqueous-phase Fe-MJ was obtained by separating the supernatant medium from macrophage cells via the centrifugation with 1500 r.p.m for 5 min. The aliquot of recovered supernatant was subject to $CHCl_3$ extract and HPLC analysis as described above. For measurements of the cell/aqueous-phase partition coefficient of Fe-MJ, Fe-MJ 1.0 μM was incubated into RPMI 1640 medium at 37° C. for half an hour in the presence of various concentrations of macrophage cells. Then the supernatant was separated and analyzed as described above. For the partition coefficient of MJ, prior to the HPLC analysis, a 10-fold ferric citrate excess was added into a MJ-$CH_3CN$ solution, followed by a two-hr incubation for the complete conversion from MJ to Fe-MJ. Aqueous-phase and total MJ and Fe-MJ, $C_{total}$ and $C_w$, respectively, were used to calculate $C_v/C_w$ according to the relationship: $C_v/C_w=(C_{total}-C_w)/C_w$. The partition coefficient, K was defined according to the following equation: $C_v/C_w=K \times [Cell]$, in which [Cell] is the concentration of macrophage cells (cells/ml) and $C_v$ is the amount of lipid-phase MJ or Fe-MJ.

Fluorescent confocal microscopy. Fluorescent confocal microscopy experiments were carried out using a Bio-Rad MRC 600 confocal microscope. Phenol-red-free PRMI1640 medium supplied with NaHCO$_3$ and HEPES buffer was used in all cases. Ga-MJ or MJ (2 µM) was incubated into macrophage culture with 1×10$^5$ cells/ml for 2 h. Fluorescent confocal images were taken in situ by using 364 nm excitation of MJ and Ga-MJ. Lipid-phase MJ and Ga-MJ show excellent fluorescence emissions around 364 nm, whereas aqueous-phase MJ shows no significant fluorescence. Ga-MJ/Nile-red (lipid-droplet marker) colocalization experiments were carried similarly, except for incubating 2 µM Ga-MJ and 0.1 µg/ml Nile red together. An argon laser was used to excite Nile red at 488 nm. For co-staining of Ga-MJ and fluorescence-labeled E. coli phagosomes: fluorescence-labeled E. coli were incubated into macrophage culture with 5×10$^5$ cells/ml for 24 h, during which macrophages were centrifuged down and then resuspended twice to increase phagocytosis of E. coli. Finally, macrophages were separated from medium and suspended E. coli, and then diluted to 1×10$^5$ cells/ml. Ga-MJ (2 µM) was added and incubated for another two hrs. Fluorescent confocal images were taken in situ by using the laser UV line at 364 m to excite Ga-MJ and the 488 nm line to visualize phagosomes labeled with fluorescent E. coli.

Figure 1A:
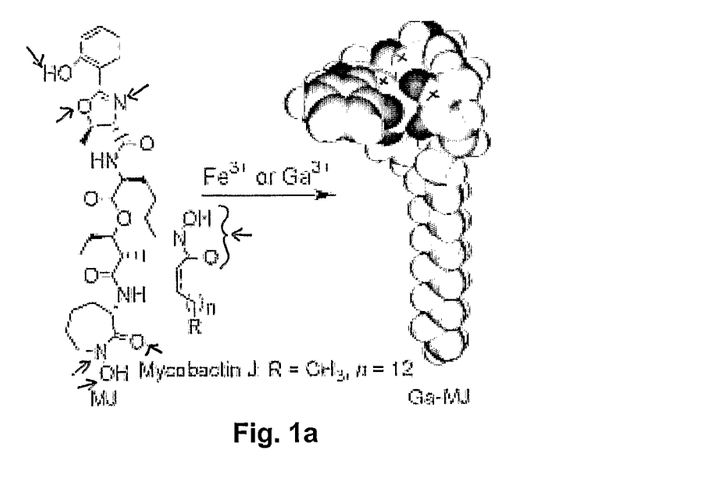
Figure 1B:
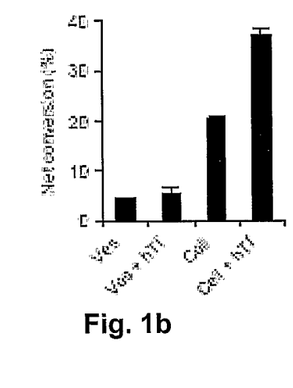

Results:

The interactions of mycobactin J, a siderophore from M. paratuberculosis (MJ, 1, FIG. 1a), with human macrophage cells in culture was examined by monitoring the appearance of MJ iron complex (Fe-MJ, 2). Approximately 20% of the added MJ was recovered as Fe-MJ under these conditions, in contrast to less than 5% conversion in the absence of macrophages (FIG. 1b). This result indicates that extracellularly added MJ translocated through the plasma membrane and acquired intracellular iron from macrophages. Similar conversion to Fe-MJ was observed in the presence of a 30-fold excess of the water-soluble iron(III) chelator desferrioxamine, confirming that this MJ-mediated iron chelation is an intracellular process.

Figure 1C:
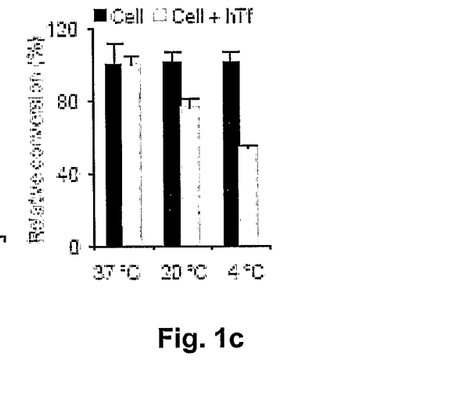
(FIG. 1c) The temperature effect on MJ-mediated iron acquisition. Iron transfer from macrophages to MJ was insensitive to temperature, but hTf-triggered iron transfer was inhibited at low temperatures. 100% "Relative conversion (%)" was defined as the conversion to Fe-MJ at 37° C., either in the presence (gray column) or absence (black column) of 10 µM hTf, respectively.

The iron transport protein transferrin is known to promote the growth of mycobacteria (Olakanmi et al., 2002, supra). It was observed that added human transferrin (hTf) stimulated MJ-mediated iron acquisition from macrophages at low, physiologically significant levels (10 µM hTf) (Sun, H. Z. et al., 1999, Chem. Rev. 99, 2817-2842). The conversion of MJ to Fe-MJ nearly doubled in the presence of hTf (FIG. 1b). This hTf-triggered conversion was significantly suppressed at low temperatures (gray columns in FIG. 1c), reaching a level at 4° C. similar to that observed in the absence of hTf (comparing FIG. 1b with FIG. 1c).

Figure 1D:
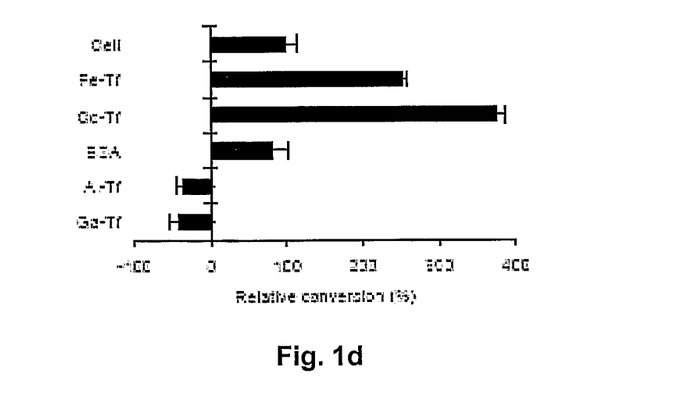

Cobalt(III) transferrin (Co-Tf) was a more effective agonist than hTf for triggering iron release from macrophages to MJ (FIG. 1d). This result suggests that initiating transferrin receptors also mobilized internal iron stores for this MT-mediated iron acquisition. By contrast, the more labile Ga(III) and Al(III) transferrin complexes not only failed to stimulate ferric release from macrophages to MJ, but also greatly suppressed the basal recovery of Fe-MJ (FIG. 1d).

Figure 2A:
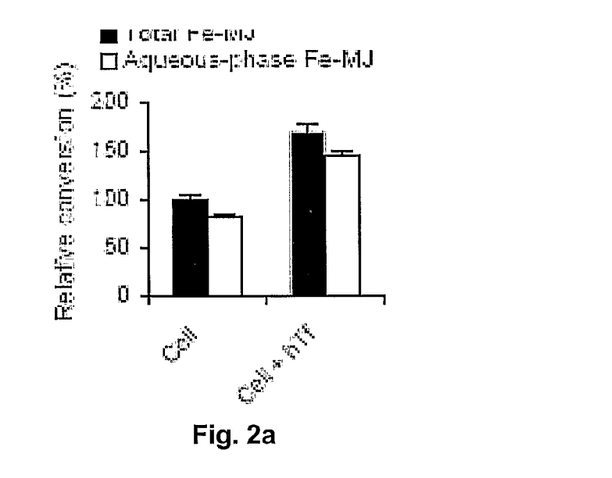
(FIG. 2a) The cell-aqueous-phase distribution of Fe-MJ upon iron release to MJ. Both aqueous-phase Fe-MJ (gray column) and total Fe-MJ (black column) were recovered after the 24-hr incubation of MJ in macrophage culture ($1 \times 10^5$ cells/ml), either in the presence ("Cell+hTf") or absence ("Cell") of hTf. Here, Fe-MJ from the aqueous phase accounted for 80% of the total recovered Fe-MJ. The total conversion in the absence of hTf was set as 100% "Relative conversion (%)".
Figure 2B:
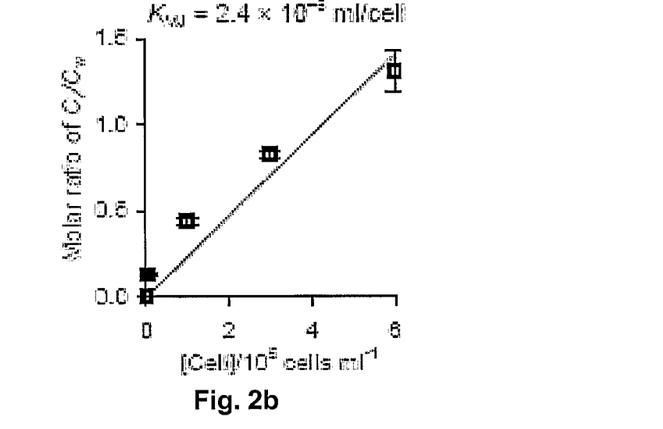
(FIG. 2b), (FIG. 2c) Measurements of cell-aqueous-phase partition coefficients of MJ and Fe-MJ. $C_v$ and $C_w$, stand as lipid-phase and aqueous-phase MJ or Fe-MJ, respectively. Partition coefficients of MJ and Fe-MJ were obtained with $K_{MJ}=2.4 \times 10^{-6}$ ml/cell and $K_{Fe-MJ}=9.8 \times 10^{-7}$ ml/cell ($C_v/C_w=K \times [\text{Cell}]$).
Figure 2C:
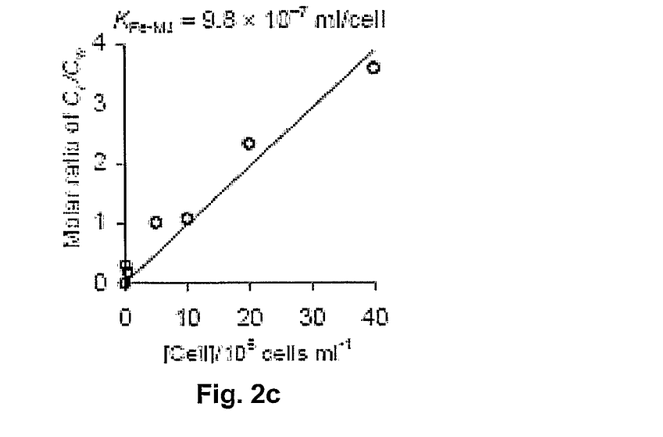

The distribution of MJ and Fe-MJ between aqueous phase and macrophages was examined by incubating MJ or Fe-MJ in 1×10$^5$ cells/ml macrophage culture for 0.5 hr. It was observed that 70-90% of the added MJ or Fe-MJ was recovered from the aqueous phase under these conditions. Both aqueous-phase Fe-MJ and total Fe-MJ after the 24-hr incubation of MJ in macrophage culture was recovered, either in the presence or absence of hTf. Here, Fe-MJ from the aqueous phase also accounted for 80% of the total recovered Fe-MJ (FIG. 2a). These observations are consistent with the cell-aqueous-phase partition coefficients for Fe-MJ and MJ of 9.8×10$^{-7}$ ml/cell and 2.4×10$^{-6}$ ml/cell, respectively (FIG. 2b and FIG. 2c). The moderate membrane affinity of Fe-MJ is also consistent with its lipid-aqueous-phase partition coefficient ($K_x$=3×10$^5$) that was obtained by using lipid vesicles as model membrane. These results indicate that MJ and its iron complex can freely diffuse among infected macrophages, mycobacteria and the medium, a feature that would facilitate access to the host iron pool and the transport of iron to the bacterial pathogens.

Figure 3A:
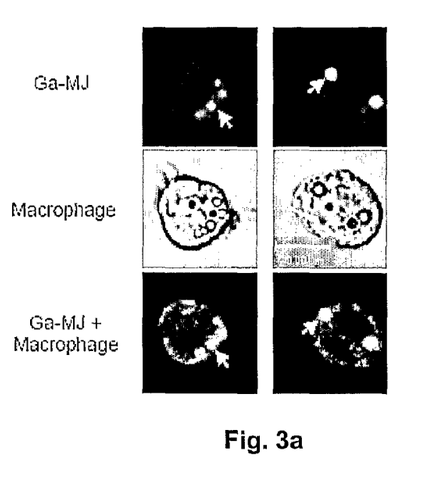
(FIG. 3a, upper left panel series) Fluorescent confocal images of the intracellular distribution of Ga-MJ in macrophages. Ga-MJ has a preferential affinity for lipid-droplets as shown by the arrows. Images from the top to bottom: Ga-MJ (green channel if figure is viewed in color), transmission images of macrophages and the overlap of both.
Figure 3B:
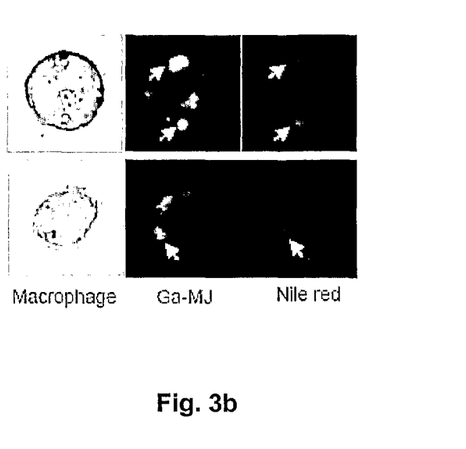
Figure 3C:
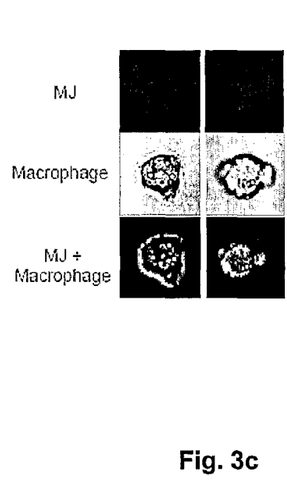
(FIG. 3c, lower left panel series) Fluorescent confocal images of the intracellular distribution of MJ in macrophages. MJ loses the lipid-droplet-affinity pattern in contrast to Fe-MJ. Images from the top to bottom: MJ (red channel if figure is viewed in color), transmission images of macrophages and the overlap of both.

To further elucidate the dynamic redistribution of added Fe-MJ and MJ within cells, fluorescent confocal microscopy was used to visualize MJ and gallium MJ complex (Ga-MJ, 3) as Fe-MJ surrogate. Lipid-phase Ga-MJ displays a pronounced fluorescence emission that was very useful for these experiments. Upon incubation in macrophage culture for 20-120 min, Ga-MJ was found preferentially localized in a single intracellular structure (FIG. 3a). This special locus was determined to be the lipid droplet by observing colocalization of Ga-MJ and Nile red in these regions (FIG. 3b). Lipid-droplets are important intracellular domains for lipid storage and sorting and for the synthesis of host-immune-defense mediator eiconsanoids (Melo, R. C. N. et al., 2003, Tissue Cell 35: 59-67; Yu, W. G. et al., 1998, Am. J. Pathol. 152: 759-769). MJ, by contrast, was homogeneously distributed among lipid regions of macrophages (FIG. 3c) similar to other hydrophobic fluorescent markers such as lysotracker (a lysosome marker) and FM 4-64 (an endo- and exocytosis marker). Consequently, this unusual affinity of Ga-MJ for lipid droplets must be attributed to a specific interaction rather than general hydrophobic effects. Fe-MJ is expected to share this lipid-droplet affinity since gallium siderophores are good structural analogs of the corresponding ferric complexes on the basis of their similar ionic radius, charge and metal-coordinating properties (Fadeev et al., 2004, supra).

Figure 3D:
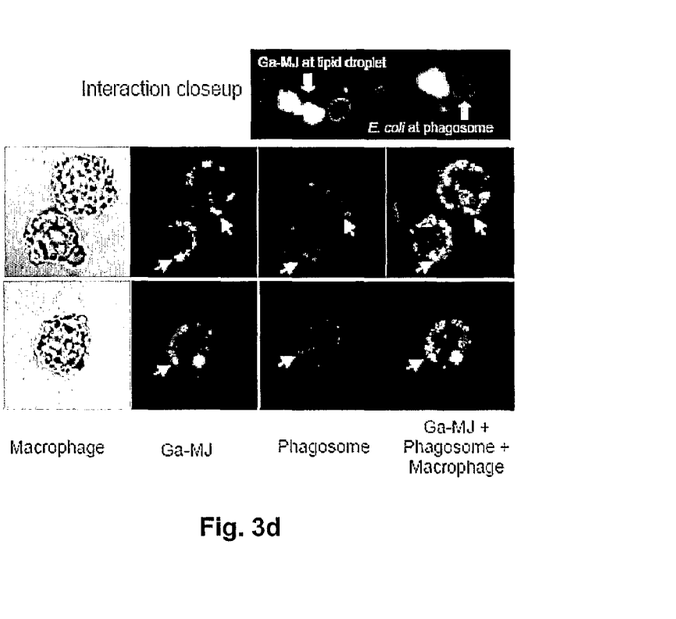

It was also observed that Ga-MJ-laden lipid droplets displayed direct contacts with phagosomes containing fluorescent E. coli (FIG. 3d). This finding indicates that host lipid trafficking has been exploited by mycobacteria for mycobactin-mediated iron delivery by recruiting Fe-MJ to lipid droplets within macrophages. The subsequent migration of Fe-MJ-laden lipid droplets to phagosomes would thus facilitate iron delivery to phagosomal mycobacteria. During bacterial infection and following phagocytosis, lipid droplets in human lung macrophages are reported to move to phagosomes and discharge their contents there (Murphy, D. J., 2001, Prog. Lipid Res. 40: 325-438; Dvorak, A. M. et al, 1983, J. Immunol. 131: 2965-2976). This lipid droplet trafficking by the host immune defense appears to be the vector for iron delivery to macrophage-niched mycobacteria.

SUMMARY

Three lines of evidence show that MJ and Fe-MJ rapidly translocate through cell membranes and maintain a dynamic distribution between the medium and cellular lipid components. First, extracellularly added MJ acquires intracellular iron from macrophages and a large portion of Fe-MJ was recovered from the aqueous phase (FIGS. 1b and 2b). Second, both MJ and Fe-MJ showed only moderate cell-aqueous-phase partition coefficients (FIG. 2b-c). Third, upon the incubation of extracellular MJ and Ga-MJ with macrophages, the diffusion of the two amphiphiles reached equilibrium within 20 minutes, with the Ga-MJ being rapidly translocated to intracellular lipid-droplets (FIG. 3a-b). Lipophilic mycobactins have been recovered both from M. tuberculosis cells and growth media (De Voss et al., 2000, supra), consistent with mycobactin diffusion. Similar diffusive properties have been reported for a variety of amphiphilic siderophores (Xu, G., et al., 2002, *J. Am. Chem. Soc.* 124: 13408-13415; Luo et al., 2005, supra). Mycobactin derivatives have also been shown recently to be antigens for activated T cells (Moody, D. B. et al., 2004, *Science* 303: 527-531).

Macrophages are responsible for clearing senescent red blood cells and thus are often richly loaded with iron. Macrophage ferric loading is even more serious during infection because approximately 30% of the circulating iron is withdrawn from serum to macrophages under such conditions. Since the experiments set forth above have shown that extracellularly added MJ can chelate macrophage-intracellular iron (FIG. 1), it appears that this intracellular iron(III) pool is accessed by lipophilic mycobactins, due to their ready diffusibility and membrane permeability. The iron source could be ferritin or intracellular-organelle-bound iron (Mulero, V. & Brock, J. H., 1999, *Blood* 94: 2383-2389).

In the presence of hTf or Co-Tf, MJ-mediated iron acquisition from macrophages was further stimulated (FIG. 1). This increased iron release to MJ must be a metabolically accelerated process, because it was completely suppressed at lower temperatures. In the presence of hTf, two components contributed to the total iron release to MJ: hTf-independent iron acquisition from the macrophage-intracellular iron pool and the hTf-stimulated iron release. For the latter, the possibility that lipophilic MJ directly mobilized iron from hTf was ruled out, since the iron transfer from hTf to mycobactin in vitro is a slow process (FIG. 1b). Furthermore, Co-Tf was even a better agonist than hTf for this stimulation process. For these reasons, it may be concluded that MJ mobilizes iron from pre-existing intracellular sources and that this process is further promoted by hTf, presumably involving hTf-receptor interactions.

EXAMPLE 2

Transfer of Ga-MJ to *Mycobacteria* in Infected Macrophage

The non-pathogenic *Mycobacterium smegmatis* (a common soil bacterium) is utilized to observe the transfer of Ga-MJ from lipid droplets to the bacteria in the macrophage phagosomes. *M. smegmatis*, to be purchased from American Type Culture Collection (ATCC), is cultured in Middlebrook's 7H9 broth medium (Difco) and nutrient broth (Difco) supplemented with 0.5% glucose and 0.05% Tween 80. The cultures are maintained at 37° C. on a shaker at 220 rpm, and sub-cultured everyday in fresh medium for 7-10 days before their use in infection studies and growth. Prior to macrophage (THP-1) infection, the bacteria are washed with phosphate-buffered saline (saline) twice and re-suspended in DMEM medium. The bacterial suspension is then added to a suspension of macrophage cells in a small Petri dish for 1 hour, after which gentamicin is added to kill any bacteria not ingested by the macrophage cells. The infected macrophage cells are fixed on a glass slide with polylysine and monitored under a confocal microscopy. The lipid droplets are labelled with Nile Red, and the bacteria are labeled with lipid stain FM5-95. Bacterial cell viability is monitored by standard techniques to observe growth inhibition by the siderophore complex.

EXAMPLE 3

Protocol for Production of Mycobactic Acid from Mycobactin

The method of Snow (1965, supra) was found to be unsuitable for isolating small quantities of mycobactic acid. A more effective protocol was developed, and is set forth below.

Materials

Porcine liver esterase (a carboxyl esterase) was purchased as an ammonium sulfate suspension (3.2 M, pH 8) from Sigma. Porcine pancreas esterase (a cholesterol esterase) was purchased as a lyophilized powder from Worthington Biochemical Corporation. Mycobactin J was prepared from ferric mycobactin J via acid washing as described above. HEPES buffer was prepared as a solution of HEPES (100 mM), NaCl (150 mM) and NaHCO$_3$ (11.5 mM) and adjusted to pH 7.6 (23° C.) with NaOH.

Chemical Hydrolysis of Mycobactin J

To a solution of mycobactin J (30 mg, 35.6 μmol) in chloroform (2 mL) was added methanol (20 mL) and aqueous NaOH (8 mL, 5 M). The mixture was allowed to stir at ambient temperature for 1 h, after which aqueous HCl (5 M) was added until the solution pH was 3. Methanol was removed in vacuo, and the aqueous residue was extracted with dichloromethane (3×10 mL). The dichloromethane layer was reduced to 5 mL and aqueous ferric chloride (5 mL, 1 M) was added to complex mycobactic acid as ferric mycobactate J. The dichloromethane layer was then washed with water (3×5 mL) to remove excess ferric chloride and cobactin J.

Ferric mycobactate J was washed with aqueous HCl (5 M) to discharge it of iron. The dichloromethane extract was washed with water (3×5 mL) and dried with Na$_2$SO$_4$ for 2 h. The dichloromethane layer was decanted and evaporated in vacuo to yield mycobactic acid as a cream-white solid.

A comparison of the $^1$H NMR spectra of mycobactin and mycobactic acid, through the absence of characteristic peaks that belong to cobactin J, demonstrated that the above procedure yielded mycobactic acid.

From δ(6-12), one amide (3) and hydroxamic acid (6) protons are absent, which is replaced by a carboxylic acid proton at δ12.60. From δ(3-5), the protons corresponding to (4) and (5) are absent. From δ(0-3), the triplet (1) and the doublet (2) are missing as well. In addition, the extent of hydrolysis of mycobactic acid was also checked with HPLC-ESI. This procedure provides mycobactic acid with less than 0.1% mycobactin.

Enzymatic Hydrolysis of Mycobactin J

To a solution of porcine liver esterase (0.1 mg) in HEPES buffer (500 μL) was added mycobactin J (5 μL, 50 mM in DMSO) with stirring at ambient temperature. After 1 h, the solution pH was adjusted to 3 with aqueous HCl (5M). The solution was extracted with chloroform (3×250 mL) and the combined chloroform extract was evaporated. The residue was re-dissolved in acetonitrile and analyzed by HPLC-MS. Similarly, porcine pancreas esterase (0.1 mg) was tested for its ability to hydrolyze mycobactin J. HPLC-MS demonstrated that more than 90% of mycobactin J was hydrolyzed in each case.

The present invention is not limited to the embodiments described and exemplified above, but is capable of variation and modification within the scope of the appended claims.

What is claimed:

1. A method of identifying compounds that interfere with mycobactin-mediated iron acquisition by mycobacteria within phagosomes of host cells, wherein interference with the mycobactin-mediated iron acquisition results from interference with one or more of: transport of apo-mycobactin across phagosome membranes into the host cytoplasm, formation of ferric mycobactin complexes in the host cytoplasm, accumulation of ferric mycobactin complexes in lipid droplets, or delivery of ferric mycobactin complexes to phagosomes from lipid droplets, the method comprising the steps of:
   a) exposing a first set of host cells, in the absence of a test compound, to an isolated mycobactin component selected from apo-mycobactin, ferric mycobactin complex, or a ferric mycobactin complex analog or derivative that binds to lipid droplets, under conditions that permit entry of the mycobactin component into the host cell cytoplasm, formation of ferric mycobactin complexes within the host cells, accumulation of ferric mycobactin complexes in lipid droplets and delivery of ferric mycobactin complexes to phagosomes from lipid droplets;
   b) exposing a second set of host cells, in the presence of the test compound, to the isolated mycobactin component of step a) under equivalent conditions as applied in step a);
   c) measuring in each of the first and second sets of host cells the amount of one or more of:
      i) mycobactin components present in the host cytoplasm;
      ii) ferric mycobactin complexes formed from apo-mycobactin;
      iii) ferric mycobactin complexes or ferric mycobactin complex analogs or derivatives associated with lipid droplets; and
      iv) ferric mycobactin complexes or ferric mycobactin analogs or derivatives present within phagosomes;
   d) comparing the measured amounts from step c) for the first and second sets of host cells; and
   e) identifying whether the test compound interfered with mycobactin-mediated iron acquisition, wherein a decrease in any of (i)-(iv) in the presence of the test compound, as compared with in the absence of the test compound, is indicative that the test compound interferes with mycobactin-mediated iron acquisition by mycobacteria within phagosomes of host cells.

2. The method of claim 1, wherein the host cells are macrophage or macrophage-like cells.

3. The method of claim 2, wherein the host cells are cultured cells.

4. The method of claim 1, wherein the mycobactin component is mycobactin J or mycobactic acid J.

5. The method of claim 1, wherein the mycobactin component is apo-mycobactin and the amount of apo-mycobactin together with ferric mycobactin complex within host cells is measured to provide a total amount of mycobactin components in the host cells, wherein a decrease in the total amount of mycobactin components in the presence of the test compound, as compared with in the absence of the test compound, is indicative that the test compound can interfere with transport of apo-mycobactin across phagosome membranes into the host cytoplasm.

6. The method of claim 1, wherein the mycobactin component is apo-mycobactin and the amount of ferric mycobactin complex within host cells is measured, wherein a decrease in amount of ferric mycobactin complex in the presence of the test compound, as compared with in the absence of the test compound, is indicative that the test compound interferes with formation of ferric mycobactin complexes in host cells.

7. The method of claim 1, wherein the mycobactin component is a ferric mycobactin complex or a ferric mycobactin complex analog or derivative that binds to lipid droplets, and the amount of ferric mycobactin complex or ferric mycobactin complex analog or derivatives accumulated in the lipid droplets is measured, wherein a decrease in the amount of ferric mycobactin complex or ferric mycobactin complex analog or derivatives accumulated in the lipid droplets in the presence of the test compound, as compared with in the absence of the test compound, is indicative that the test compound interferes with accumulation of ferric mycobactin complexes in host cell lipid droplets.

8. The method of claim 1, wherein the mycobactin component is a ferric mycobactin complex or a ferric mycobactin complex analog or derivative that binds to lipid droplets, and the amount of ferric mycobactin complex or ferric mycobactin complex analog or derivatives delivered to phagosomes is measured, wherein a decrease in the amount of ferric mycobactin complex or ferric mycobactin complex analog or derivatives delivered to phagosomes in the presence of the test compound, as compared with in the absence of the test compound, is indicative that the test compound interferes with delivery of ferric mycobactin complexes from the lipid droplets to the phagosomes.

9. The method of claim 1, wherein the mycobactin component is a ferric mycobactin complex analog or derivative selected from gallium-mycobactin or gallium-mycobactic acid.

* * * * *

UNITED STATES PATENT AND TRADEMARK OFFICE
CERTIFICATE OF CORRECTION

| | | |
|---|---|---|
| PATENT NO. | : 8,389,231 B2 | Page 1 of 1 |
| APPLICATION NO. | : 11/990718 | |
| DATED | : March 5, 2013 | |
| INVENTOR(S) | : John T. Groves | |

It is certified that error appears in the above-identified patent and that said Letters Patent is hereby corrected as shown below:

In the Specifications:

Column 1, lines 9-12, the phrase "Pursuant to 35 U.S.C. §202(c), it is acknowledged that the United States Government may have rights in the invention described herein, which was made in part with funding from the National Science Foundation, Grant No. 9810248." should read --This invention was made with government support under Grant No. CHE-9810248 awarded by the National Science Foundation. The government has certain rights in the invention--.

Signed and Sealed this
Thirteenth Day of August, 2013

Teresa Stanek Rea
*Acting Director of the United States Patent and Trademark Office*